United States Patent [19]

Alperin et al.

[11] 3,930,792

[45] Jan. 6, 1976

[54] HAIR DYEING AND CONDITIONING COMPOSITIONS

[75] Inventors: George Alperin, Stamford; Richard DeMarco, Danbury; Raymond Feinland, Stamford, all of Conn.

[73] Assignee: Clairol Incorporated, New York, N.Y.

[22] Filed: Oct. 31, 1974

[21] Appl. No.: 519,492

Related U.S. Application Data

[63] Continuation-in-part of Ser. No. 278,970, Aug. 9, 1972, abandoned.

[52] U.S. Cl. .............................. 8/10.1; 8/10; 8/85
[51] Int. Cl.² ............................................ A61K 7/13
[58] Field of Search .......................... 8/10.1, 10, 85

[56] References Cited
UNITED STATES PATENTS

| | | | |
|---|---|---|---|
| 3,555,584 | 1/1971 | Kalopissis | 8/10.1 |
| 3,577,528 | 5/1971 | McDonough et al. | 8/10.1 |
| 3,629,330 | 12/1971 | Brody et al. | 8/10.1 |

FOREIGN PATENTS OR APPLICATIONS

| | | | |
|---|---|---|---|
| 741,334 | 11/1955 | United Kingdom | 8/10.1 |
| 889,327 | 2/1962 | United Kingdom | 8/10.1 |
| 956,401 | 4/1964 | United Kingdom | 8/10.1 |
| 1,137,922 | 1/1957 | France | 8/10.1 |

*Primary Examiner*—Dale R. Ore
*Attorney, Agent, or Firm*—Irving Holtzman; George A. Mentis; David J. Mugford

[57] ABSTRACT

A semi-permanent hair dye composition that simultaneously dyes and conditions hair to make it more manageable including a direct dyeing nitro dye capable of dyeing hair, certain quaternary amine compounds and certain N-oxyalkylated fatty acid amides.

15 Claims, No Drawings

HAIR DYEING AND CONDITIONING COMPOSITIONS

RELATED CASES

This application is a continuation-in-part of application Ser. No. 278,970 filed Aug. 9, 1972 now abandoned.

This invention relates to nitro-dye containing hair dye compositions of the so-called semi-permanent type which are designed to impart color to human gray hair and/or pigmented hair with a semi-permanent fastness. The nitro-dye containing semi-permanent hair dye compositions are to be distinguished from oxidation dye compositions in that the former are of the direct dyeing type and do not require an oxidizing agent for the development of their color. They are further to be distinguished from the temporary hair dye rinses in which the color, after application to the hair is washed out with relative ease. They are also unlike basic dye hair dye compositions which are characterized by the fact that the basic dyes which comprise the chief coloring component tend to be unstable in water and to give skin staining.

Nitro-dye hair dye compositions of the semi-permanent type mentioned above are widely used commercially both in the home and in beauty salons. These have gained wide acceptance because of their effectiveness and because of their ease of application. However, their use has often been accompanied by the disadvantage that after their application the hair when wet has a tendency to snarl. Moreover, when dried after application of these dye compositions the manageability of the hair becomes a problem and the condition of the hair leaves something to be desired.

It has now been found that the above-noted disadvantages may be substantially eliminated by incorporating in said semi-permanent hair dye compositions a hair substantive quaternary amine compound and an N-oxyalkylated long chain fatty acid amide as hereinafter described. It has been more particularly found that by including both of these materials in said hair dye compositions that products are obtained which when applied to hair prevent the hair from snarling when wet and improves the combability of the hair. Moreover, after application of this product to the hair and drying, the hair is more manageable. There is also an improved sheen and texture imparted to the hair when compared with hair which has been given a treatment with products not containing this combination of materials.

It is, accordingly, an object of this invention to provide nitro-dye hair dye compositions of the semi-permanent type in which hair snarling and unmanageability after use are reduced to a minimum and which improves the sheen and texture of the hair.

It is also an object of this invention to provide a process which employs such hair dye compositions.

It is another object of this invention to provide nitro-dye hair dye compositions of the semi-permanent type which have incorporated therein a hair-substantive quaternary amine compound and a hair-substantive N-oxyalkylated long chain fatty acid amide as hereinafter defined.

It is still another object of this invention to provide a process for simultaneously imparting to human hair, living or otherwise, semi-permanent color and at the same time greater combability, manageability, improved condition and sheen by applying a nitro-dye hair dye composition containing a hair-substantive quaternary amine compound and a hair-substantive N-oxyalkylated long chain fatty acid amide.

Other and more detailed objects of this invention will be apparent from the following description and claims.

It is known prior art to include certain quaternary amine compounds in nitro-dye containing hair dye compositions for the purpose of dispersing the ingredients contained in these compositions and to facilitate the application of dye. By way of illustration, mention may be made of U.S. Pat. Nos. 3,119,867; 3,634,478 and 3,642,423. However, these patents were not concerned with the problems toward which the present invention is directed; namely, the improvement of the condition, manageability, combability, etc. as described above. The quaternary amine compounds are used in these patents for a totally different purpose. Moreover, as will become clearer from the discussion below, these patents do not employ the particular class of quaternary amine compounds which have been found to be particularly advantageous for use in the present context. Furthermore, these patents do not teach the use of the combination of the quaternary amine compounds together with the N-oxyalkylated fatty acid amides which is characteristic of the present invention, nor the advantages attending the use of this combination.

It has also been suggested in U.S. Pat. No. 3,369,970 that certain cationic surface-active agents may be included as a dispersing agent in a viscous mixture in which a powdered basic dye is distributed in the viscous carrier. Among the surfactants mentioned for use in this patent are included cationics such as cetyltrimethylammonium bromide, tetradecyltrimethylammonium chloride and non-ionics such as lauric acid diethanol amide. However, this patent does not teach or suggest the use of a nitro-dye in the compositions described therein, this being a feature of the present invention. The disadvantages of using basic dyes are quite apparent from the description given in U.S. Pat. 3,369,970 e.g. instability, skin staining, etc. (See Column 1, paragraph 4). Furthermore, the basic dye compositions tend to give uneven dyeing, the dye uptake being greater along certain portions of the hair shaft than others. Moreover, this patent does not teach use of the combination of quaternary amine compounds and N-oxyalkylated fatty acid amide which forms part of the instant invention nor the advantages flowing from this use. Finally, the function which this combination of quaternary amine compound and N-oxyalkylated fatty acid amide has in the present compositions is not taught at all in this patent.

It is further shown in the prior art to include in hair rinse compositions certain quaternary amine compounds as hair conditioning agents. This is exemplified by such U.S. Pat. Nos. as 3,155,591 and 3,272,712. These patents, however, do not suggest that it would be possible or even feasible to advantageously incorporate such quaternary amine compounds in a nitro-dye containing composition of the semi-permanent type nor whether the conditioning function of the quaternary amine compound could be carried over into such a composition. Furthermore, there is no teaching in these patents of the use of the combination of the quaternary amine compounds employed in this invention together with the N-oxyalkylated fatty acid amide utilized herein nor the advantages attending the same.

As mentioned above, it is a feature of the present invention to incorporated in nitro-dye semi-permanent hair dye compositions of interest certain hair-substantive quaternary amine compounds. These will be hair-substantive and non-toxic compounds described by the formula:

(1)
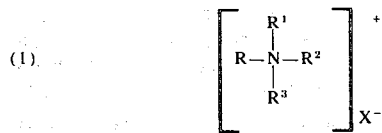

wherein $R^1$, $R^2$ and $R^3$ are alkyl radicals having 1 to 3 carbons and preferably 1 carbon atom; R is a long chain hydrocarbon radical having from 12 to 24 carbon atoms and preferably from 16 to 18 carbon atoms; and $X^-$ is an anion. The anion can be any one of a large variety of anions which are known in the prior art to be capable of forming part of a quaternary amine compound. Illustrative, but not limitative, of the anions which may have the value of X in formula (1) mention can be made of hydroxide (i.e. $OH^-$) halide (e.g. chloride, bromide, iodide, fluoride); sulfate, nitrate; $-SO_4CH_3$; phosphate, acetate, sulfonate, etc. Equally useful for the purposes of the present invention are the compounds of formula (1) above in which the anion X is ethyl sulfate (i.e. $-SO_4C_2H_5$). The ethyl sulfate anion is an equivalent for the anions already listed above in defining anion X.

It is within the purview of the present invention to include one or more quaternay amine compounds falling within formula (1) in said semi-permanent hair dye compositions. As a matter of fact, some of the commercially available quaternary amine compounds that are useful herein, in fact, constitute mixtures of compounds falling within formula (1) in which, for example, the value of R for each such compound in the mixture is a hydrocarbon radical having from 16 to 18 carbon atoms.

$R^1$, $R^2$ and $R^3$ in formula (1) above may be the same or a different alkyl radical. Illustratively, they may be methyl, ethyl, n-propyl or isopropyl. By way of further illustrating the hydrocarbon radical R in formula (1) mention may be made of lauryl, myristyl, n-hexadecyl, oleyl, n-octadecyl, n-octadecenyl, n-octadecadienyl, arachidyl, behenyl, lignoceryl, etc. More specifically to illustrate particular quaternary amine compounds that are useful herein, mention may be made of lauryltrimethylammonium chloride, -bromide and -iodide; hexadecyltrimethylammonium chloride; octadecyltrimethylammonium chloride; octadecenyltrimethylammonium chloride; octadecadienyltrimethylammonium chloride; laurylmethyldiethylammonium sulfate; n-hexadecyldimethylethylammonium nitrate; octadecyltrimethylammonium acetate, lauryldimethylethylammonium ethyl sulfate, etc. and mixtures thereof.

The quantity of quaternary amine compound that may be incorporated in the hair dye compositions of this invention will vary depending upon the other ingredients contained in the composition as well as the results desired. Ordinarily, however, it will constitute between about 0.1% and 3.0% by weight of the total composition.

As also mentioned above, it is another feature of the present invention to incorporate in said nitro-dye hair dye compositions a hair-substantive N-oxyalkylated long chain fatty acid amide together with the aforesaid quaternary amine compound. The N-oxyalkylated fatty acid amides that are useful herein are defined as hair-substantive non-toxic compounds of the formula:

(2)
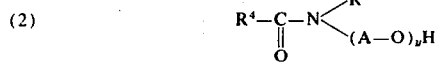

in which:
a. $R^4$ is a long chain hydrocarbon radical having from 12 to 24 carbon atoms and preferably 16 to 18 carbon atoms;
b. $R^5$ is hydrogen or the radical $(A'-O)_xH$; and in which:

A and A' are the same or different and are divalent alkylene radicals having 2 to 4 carbon atoms; and x and y are the same or different and are whole numbers from 1 to 100. By way of illustration, A and $A^1$ in formula (2) may be dimethylene ($-CH_2-CH_2-$); trimethylene ($-CH_2-CH_2-CH_2-$); isopropylene

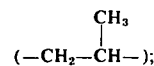

tetramethylene ($-CH_2-CH_2-CH_2-CH_2-$). Further by way of illustration, $R^4$ in formula (2) above may be lauryl, myristyl, palmityl, stearyl, behenyl, oleyl, linolyl, linolenyl, etc. It is also within the scope of this invention to employ a mixture of N-oxyalkylated fatty acid amides falling within formula (2) above. Several commercially available products that are useful herein are, in fact, of this character.

In a preferred form of this invention, the N-oxyalkylated fatty acid amide is of the polyoxyethylated type. These may best be described by the formula:

(3)
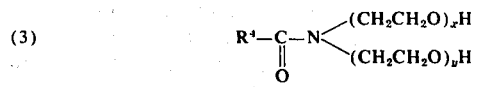

in which $R^4$ has the same value ascribed to it above in connection with formula (2) and x and y are numbers, the sum of $x + y$ being in the range of from 40 to 100. These materials have a virtue in that they are water soluble and tend to keep the product as a homogeneous product.

To illustrate more specifically the N-oxyalkylated fatty acid amides that are useful for the present purposes, mention may be made of the following: lauric -monoethanol and -diethanol amide; stearyl -monoethanol and -diethanol amide; palmityl monoethanol and diethanol amides; compounds of formula (3) in which (a) $R^4$ = oleyl, $x + y$ = 5; (b) $R^4$ = stearyl, $x + y$ = 5; (c) $R^4$ = palmityl, $x + y$ = 5; (d) $R^4$ = myristyl, $x + y$ = 5; (e) $R^4$ = linoleyl, $x + y$ = 5 and mixtures thereof; also compounds of formula (3) in which (f) $R^4$ = oleyl, $x + y$ = 50; (g) $R^4$ = stearyl, $x + y$ = 50; (h) $R^4$ = palmityl, $x + y$ = 50; (i) $R^4$ = myristyl, $x + y$ = 50; (j) $R^4$ = linoleyl, $x + y$ = 50 and mixtures thereof. Ethomid HT-60 is an example of a commercial product that is useful as the N-oxyalkylated fatty acid amide herein. This is prepared by the ethoxylation of tallow fatty acid amides with 50 moles of ethylene oxide. This may further be described as a mixture of amides of formula (3)

above in which $R^4$ is (37–43%) oleyl, (24–32%) palmityl, (20–25%) stearyl, (3–6%) myristyl and (2–3%) linoleyl; and the sum of $x + y$ is equal to about 50. Among other N-polyoxyethylated fatty acid amides that are useful herein, mention may be made of oleyl

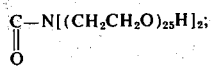

palmityl

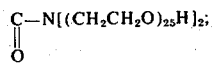

stearyl

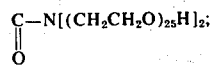

myristyl

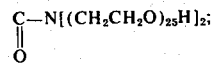

linoleyl

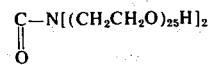

and mixtures thereof.

The particular quantity of N-oxyalkylated fatty acid amide that will be contained in the hair dye compositions of this invention will vary depending upon the relative quantities of other ingredients and the particular results that are sought after. In general, however, this will constitute between about 0.2% to 3.5% by weight based on the total weight of the composition.

An essential component of the compositions of this invention is the direct dyeing nitro-dye. This generally gives the composition its character as a semi-permanent hair dye composition, largely because of its good affinity for hair when applied at ambient temperatures. There are a large number of direct dyeing nitro-dyes that are known in the prior art that may constitute the nitro-dye component of this composition either alone or in combination. In this connection, attention is directed to the following U.S. Pat. Nos.: 2,750,326; 2,750,327; 2,983,651; 3,049,393; 3,088,978; 3,168,442; 3,088,877; 3,119,867; 3,088,878; 3,488,138, 3,634,478; 3,642,423; 3,632,582 and 3,591,638. Of special interest are the direct dyeing nitro aminobenzene dyes series. As is evident from the terminology, the nitro aminobenzene dyes have a benzene nucleus which is substituted by both a nitro and an amino group. The benzene nucleus of such dyes can contain more than one nitro group, such as up to three nitro groups, more than one amino group, such as up to three amino groups, and can further be substituted with from 1 to 3 hydroxyls and with from 1 to 3 lower aliphatic radicals. Illustrative of the lower aliphatic radicals which can be substituted on the benzene nucleus, there can be mentioned alkyls and hydroxyalkyls. The amino group or groups can be primary or can be substituted with various aliphatic or aryl radicals to form secondary or tertiary amines. Illustrative of the amino substituents, there can be mentioned lower aliphatic radicals such as alkyls, hydroxyalkyls, carboxyalkyls, polyalkylene-glycol radicals, and the like. The aryl amino substituent can be phenyl or substituted phenyl.

A type of preferred nitroaminobenzene dye can be represented by the formula:

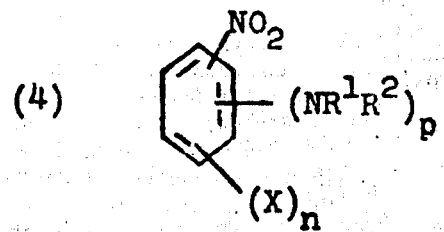

wherein each of $R^1$ and $R^2$ is hydrogen, or lower aliphatic e.g. containing 1 to 8 carbon atoms, phenyl or substituted phenyl; $p$ is an integer from 1 to 2; X is hydroxyl, nitro, chlorine, lower alkyl or lower alkoxy or $NR^1R^2$; $n$ is an integer from 0 to 1; and $n + p$ is 1 to 3 and preferably 1 to 2.

To further illustrate the nitroaminobenzene dyes that may be used in this invention, the following can be mentioned:

1. $N^4,N^4$-bis-(2'-hydroxyethyl)-$N^1$-methyl-2-nitro-p-phenylenediamine
2. $N^1,N^4,N^4$-tris-(2'-hydroxyethyl)-2-nitro-p-phenylenediamine
3. $N^1$-(2'-hydroxyethyl)-2-nitro-p-phenylenediamine
4. N(2'-hydroxyethyl)-2-nitroaniline
5. N,N-bis(2'-hydroxyethyl)-2-amino-5-nitrophenol
6. 2-nitro-p-phenylenediamine
7. 4-nitro-o-phenylenediamine
8. 1-anilino-4-amino-2-nitrobenzene
9. 1-methylamino-2-amino-4-nitrobenzene
10. 1-ethylamino-4-amino-2-nitrobenzene
11. 1-(2'-hydroxyethylamino)-2-amino-4-nitrobenzene
12. 1-[2'-(2''-hydroxyethoxy)ethylamino]-4-amino-3-nitrobenzene
13. 1,4,bis-(2'-hydroxyethylamino)-2-nitrobenzene
14. 1-(2',3'-dihydroxypropylamion)-4-amino-3-nitrobenzene
15. 1-methylamino-4-amino-2-nitrobenzene
16. 1-methylamino-4-[2''-hydroxyethoxy)ethylamino]-2-nitrobenzene
17. 5-nitro-2-aminophenol
18. 4-nitro-2-aminophenol
19. 2-nitro-4-aminophenol
20. 4-nitro-2-(2'-hydroxyethylamino)phenol
21. N-(p-nitrophenyl)glycine
22. N-(2-hydroxy-5-nitrophenyl)glycine
23. 1-methylamino-2-nitro-4-propylaminobenzene
24. 1-methylamino-2-nitro-4-hydroxymethylaminobenzene
25. 1-methylamino-2-nitro-4-(3'-hydroxypropyl)aminobenzene 26  1-methylamino-2-nitro-4-(2',3'-dihydroxypropyl)aminobenzene
27  1-methylamino-2-nitro-4(4'-hydroxybutyl) aminobenzene
28  1-hydroxymethylamino-2-nitro-4-methylaminobenzene
29  1-(3'-hydroxypropyl)amino-2-nitro-4-methylaminobenzene
30  1-(2',3'-dihydroxypropyl)amino-2-nitro-4-methylaminobenzene
31  1-hydroxymethylamino-2-nitro-4-ethylaminobenzene
32  1-(2'-hydroxyethyl)amino-2-nitro-4-ethylaminobenzene
33  2-nitro-5-methoxy-p-phenylenediamine
34  5-methyl-2-nitro-p-phenylenediamine
35  5-chloro-2-nitro-p-phenylenediamine The quantity of nitro-dye or nitroaminobenzene dye that will be contained in the compositions of this invention will vary depending on the shade desired and the quantity and nature of the other components. All that is required is that a tinctorially effective amount of the dye be employed. Ordinarily, this will comprise about 0.01% to 3.0% by weight based on the total weight of the composition.

Aside from the aforesaid components, the composition of this invention may contain other components which are ordinarily contained in nitro-dye containing semi-permanent hair dye compositions. Thus, the major component of these compositions is usually water and consequently they will ordinarily be aqueous compositions. The quantity of water contained in these compositions will vary depending upon the quantity and types of other ingredients. Usually, however, it will constitute between 80% and 99.7% by weight of the composition.

The pH of the present dye compositions can vary widely e.g. from about 2.5 to 11. It is preferred, however, that the present dye compositions be in the acid range, and particularly at a pH of about 4.5 to 6.5. The pH of the compositions may be adjusted with any inorganic or organic acid or acid salt which is compatible with the composition. As illustrative of these acids or acid salts there can be mentioned: sulfuric, formic, acetic, lactic, citric or tartaric acid, or ammonium sulfate, sodium dihydrogen phosphate, or potassium bisulfate. When using citric acid, the weight percent of the composition can vary from about 0.1 to 2.0% and preferably from about 0.4 to 0.6%.

In adjusting the pH of the composition, particularly in the alkaline range, a variety of alkalizing agents can be used, e.g. ammonia, alkali or alkaline earth metal hydroxides, amines, etc. The quantity of the alkalizing agent employed can vary over a wide range, depending on the dye and the particular alkalizing agent employed and the pH desired. Illustratively, the alkalizing agent can vary from about 0.1% to about 2.0% and preferably from about 0.3% to about 1.2% by weight of the composition.

The alkalizing agents of choice, however, are water-soluble organic amines of low volatility (b.p. higher than about 50°C), having less than about 12 carbon atoms, such as n-propylamine, isobutylamine, 2-ethylbutylamine, diethylamine, diethylamine, triethylamine. Particularly, suitable are the following: (A) primary aliphatic diamines, such as ethylenediamine; 1,2-diaminopropane; 1,3-diaminopropane; diethylenetriamine; triethylenetetramine; 2,2'-iminodipropylamine; 3,3'-iminodipropylamine; and bis-hexamethylenetriamine; (B) alkanolamines, such as ethanolamine; isopropanolamine; diethanolamine; di-isopropanolamine; triethanolamine; triisopropanolamine; N-methyldiethanolamine; diisopropylethanolamine; dimethylisopropanolamine; 2-amino-2-methylpropane-1,3,diol; tris(hydroxymethyl)methylamine and the like, which may also have a phenyl substituent, e.g. N(2-hydroxyethyl)aniline; N-methyl-N(2-hydroxyethyl)aniline; N,N-bis(2-hydroxyethyl)aniline; and (C) heterocyclic amines, such as morpholine, N-methylmorpholine, N-ethylmorpholine, N-hydroxyethylmorpholine, N-phenylmorpholine, piperidine, N-hydroxyethylpiperidine, and piperazine.

A thickening agent can also be incorporated in the dyeing compositions of this invention which may be one of several of those commonly used in hair dyeing, such as gum arabic, or cellulose derivatives, such as methylcellulose e.g. Methocel 60HG, or hydroxyethylcellulose e.g. Cellosize QP-40, or acrylic polymers, or inorganic thickeners, such as bentonite. The quantity of this thickening agent can vary over a wide range, such as that of from about 0.1% to 8.0%, but preferably will be in the range of from about 0.5% to 5% by weight.

The dyeing compositions of this invention, as mentioned above, will ordinarily be aqueous compositions. The term "aqueous composition" is used herein in its usual generic sense as embracing any water-containing composition useful for the present purposes. This includes true solutions of the dye in an aqueous medium, either alone or in conjunction with other materials which are also dissolved or dispersed in the aqueous medium. The term "aqueous composition" also encompasses any mixture of dye with the aqueous medium either alone or together with other ingredients. The dye may be colloidally dispersed in the medium or may merely be intimately mixed therein.

The term "aqueous medium" as used herein, includes any medium which contains water. Thus, the aqueous medium may be an aqueous alkaline, aqueous neutral or aqueous acid medium. Moreover, the aqueous medium may comprise water and a solvent, e.g. ethanol. The latter may be employed as a common solvent to enhance the solution of the dye or some other organic material.

Typical dyeing compositions of the various classes described above are set forth below:

TABLE I

| ACID COMPOSITIONS | General Range | Preferred Range |
| --- | --- | --- |
| Nitro-dye | 0.01% to 3.0% | 0.2% to 0.4% |
| Quaternary Amine | 0.1 % to 3.0% | 1.5% to 2.0% |
| N-oxyalkylated Fatty Acid Amide | 0.2 % to 3.5% | 2.0% to 3.0% |
| Thickening Agent | 0.1 % to 8.0% | 1.5% to 2.0% |
| Adjust pH to | 3.0 to 7.0 | 4.5 to 6.5 |
| Water QS to 100 | | |

When citric acid is employed in the compositions of Table I, the general range will be about 0.1% to 2.0% by weight and the preferred range will be about 0.4% to 0.6%. In this event, sufficient alkali may then be added to adjust the pH of the compositions within the range specified.

Any of the dyes, surface active agents, alkalies, thickening agents, acids and combinations thereof set forth above may be used in the proportions specified in the

ALKALI COMPOSITIONS

The alkali compositions are similar to the above acid compositions, except that alkali is in excess over acid, and the alkali is added to a pH of 7–11, preferably 8.0–9.0.

The dyeing compositions used in this invention can be prepared by the conventional methods used in the hair dyeing art. Thus, they can be prepared by dissolving or suspending the dye in water in the desired concentrations. Water miscible organic solvents e.g. ethanol, can be employed to facilitate solution of the dye; in this event, the dye can be dissolved first in the solvent and then diluted with water. The dispersion of the various ingredients can also be facilitated by heating the composition at temperatures varying from 40° to 110°C, either before dilution with water or afterwards.

The compositions of this invention may also take the form of aerosol compositions. In this event, the nitro-dye compositions described above and containing the quaternary amine compound and the N-oxyalkylated fatty acid amide will be contained in an aqueous phase concentrate. Any of the propellants well known to those skilled in the art may be used in this aspect of the invention.

These compositions can be applied to hair by the conventional techniques used in this art. Illustratively, when applied to living hair on the human head or otherwise, the compositions can be applied to the hair with a brush, sponge, from an aerosol container or other means of contact, such as pouring the composition directly onto the hair until saturated.

The reaction time or time of contact of the dyeing composition with the hair is not critical and can vary over a wide range used in the hair dyeing art, such as periods of about 1 minute to about 2 hours. Preferably, a period of from about 5 minutes to about 60 minutes is utilized and most often a period of 10 to 30 minutes. The dyeing temperature can vary over wide limits as is conventional in the art. Thus, the dyeing temperature can vary from about room temperature, e.g. about 20° to about 60°C and preferably from about 20° to about 45°C.

The following Examples are given to further illustrate this invention. It is to be understood, however, that they are not intended to be limitative but merely exemplary of the present invention.

The compositions given in Table II below were prepared using the following procedure:

The dyestuffs were first placed in a container and sufficient organic solvent e.g. ethyl alcohol or diethylene glycol monoethyl ether was added to said dye-stuffs to thoroughly wet them out and to form a slurry. The quaternary ammonium compound or compounds; the N-ethoxylated fatty acid amide or amides; the alkali (monoethanolamine or diethanolamine) and the citric acid were then added to the slurry. About 70% of the required water, preheated to about 70°C was then added thereto and the mixture was stirred until a uniform solution was obtained. To this was then added the thickener (methylcellulose) and the resulting mixture was again stirred for an hour while maintaining it at a temperature of between 65° to 70°C. The perfume was then added and then the remainder of the water (at room temperature) to 100% was added and the mixture stirred for ten minutes. The perfume was obviously added to give elegance to the product. It can be omitted from these compositions without influencing their effectiveness.

TABLE II

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| $N^4,N^4$-bis(2'-hydroxyethyl)-$N^1$-methyl-2-nitro-p-phenylenediamine | 0.4 | 0.4 | 0.4 | — | — | — | — | — |
| $N^1,N^4,N^4$-tris(2'-hydroxyethyl)-2-nitro-p-phenylenediamine | — | — | — | 0.4 | 0.4 | 0.4 | — | — |
| $N^1$-(2'-hydroxyethyl)-2-nitro-p-phenylenediamine | 0.01 | 0.01 | 0.01 | 0.01 | 0.01 | 0.01 | 0.16 | 0.004 |
| 1-anilino-4-amino-2-nitrobenzene | 0.01 | 0.01 | 0.01 | 0.01 | 0.01 | 0.01 | 0.12 | 0.004 |
| N,N-bis(2'-hydroxyethyl)-2-amino-5-nitrophenol | 0.07 | 0.07 | 0.07 | 0.07 | 0.07 | 0.07 | 0.16 | 0.040 |
| N(2'-hydroxyethyl)-2-nitroaniline | 0.06 | 0.06 | 0.06 | 0.06 | 0.06 | 0.06 | 0.13 | 0.060 |
| Ethyl alcohol | 5.0 | 5.0 | 5.0 | — | — | — | — | — |
| Diethylene glycol monoethyl ether | — | — | — | 5.0 | 5.0 | 5.0 | 5.0 | 5.0 |
| Hexadecyltrimethyl ammonium chloride | 2.0 | — | 1.0 | 2.0 | — | 1.0 | — | — |
| Octadecenyltrimethyl ammonium chloride | — | 1.8 | 0.9 | — | 1.4 | 0.9 | 1.5 | 1.5 |
| Octadecadienyltrimethyl ammonium chloride | — | — | — | — | — | — | 1.5 | 1.5 |
| Ethoxylated (50 Moles E.O.) oleyl diethanolamide | 2.0 | 2.0 | — | — | 1.5 | 1.0 | 2.5 | 2.5 |
| Ethoxylated (50 Moles E.O.) palmityl diethanolamide | — | — | 2.0 | 2.0 | 0.5 | 1.0 | — | — |
| Monoethanolamine | 0.4 | 0.4 | 0.4 | — | — | — | — | — |
| Diethanolamine | — | — | — | 0.71 | 0.71 | 0.71 | 0.71 | 0.71 |
| Citric Acid | 0.5 | 0.5 | 0.5 | 0.5 | 0.5 | 0.5 | 0.5 | 0.5 |
| Methyl Cellulose* | 2.0 | 2.0 | 2.0 | 2.0 | 2.0 | 2.0 | 2.0 | 2.0 |
| Perfume | 0.1 | 0.1 | 0.1 | 0.1 | 0.1 | 0.1 | 0.1 | 0.1 |
| Water | q.s. to 100% | | | | | | | |

*Methyl cellulose referred to herein and elsewhere is characterized as follows: Methoxyl content 28–30%; viscosity of a 2.0% aqueous solution at 20°C - 2700–3700 cps, average M.W. 86,000.

The dye compositions of Table II are applied to human hair (the hair may be dry or slightly wet) and are spread uniformly throughout, insuring that no areas are omitted. The compositions are allowed to remain on the hair for 10 to 30 minutes then thoroughly rinsed out of the hair with water. The hair is then allowed to dry.

The compositions of Examples 1 to 6 when applied to grey hair in the manner described above, colored it a brown shade. Moreover, the combability of the hair, when wet, was greatly improved. Upon drying, it was noted that the overall condition of the hair had improved considerably as the hair became more manageable and exhibited improved sheen and texture.

The composition of Example 7, when applied to grey hair in the manner described above, colored it an auburn shade with the same creme rinse and conditioning properties shown in Examples 1 to 6. When applied to medium or dark brown hair, it will impart color highlights with the same creme rinse and conditioning properties shown in Examples 1 to 6.

The composition of Example 8, when applied to grey hair in the manner described above, colored it a blonde shade with the same creme rinse and conditioning properties shown in Examples 1 to 6. When applied to light brown or blonde hair, it will impart color highlights with the same creme rinse and conditioning properties shown in Examples 1 to 6.

TABLE II (Cont.)

|  | Ex. 9 |
|---|---|
| $N^4,N^4$-bis(2'-hydroxyethyl)-$N^1$-methyl-2-nitro-p-phenylenediamine | 0.4 |
| $N^1$-(2'-hydroxyethyl)-2-nitro-p-phenylenediamine | 0.01 |
| 1-anilino-4-amino-2-nitrobenzene | 0.01 |
| N,N-bis(2'-hydroxyethyl)-2-amino-5-nitrophenol | 0.07 |
| N(2'-hydroxyethyl)-2-nitroaniline | 0.06 |
| Diethylene glycol monethyl ether | 5.0 |
| Lauryldimethylethylammonium ethyl sulfate | 1.1 |
| Ethoxylated (50 moles E.O.) oleyl diethanolamide | 2.7 |
| Triethanolamine | 0.9 |
| Citric Acid | 0.3 |
| Methyl Cellulose | 2.0 |
| Perfume | 0.1 |
| Water | q.s. to 100% |

The composition of Example 9 is applied to human hair in the same fashion as described above in connection with the composition of Examples 1 through 8 with comparable results.

Although the invention has been described with reference to specific forms thereof, it will be understood that many changes and modifications may be made without departing from the spirit of this invention.

What is claimed is:

1. An aqueous hair dye composition of the semi-permanent type comprising
   a. a tinctorial amount of a direct-dyeing nitroaminobenzene hair dye having good affinity for hair when applied at ambient temperatures;
   b. from about 0.1% to 3% by weight based on the total weight of the compositions of a hair-substantive quarternary amine compound of formula:

(1) 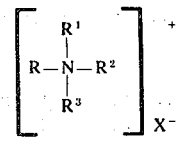

in which:
   i. $R^1$, $R^2$ and $R^3$ are alkyl having from 1 to 3 carbons;
   ii. R is a long chain hydrocarbon having from 12 to 24 carbons; and
   iii. X is an anion; and
   c. from 0.2% to 3.5% by weight based on the total weight of the composition of a hair-substantive N-oxyalkylated fatty acid amide of formula:

(2) 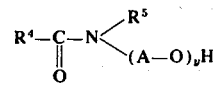

in which:
   i. $R^4$ is a long chain hydrocarbon having from 12 to 24 carbons;
   ii. $R^5$ is hydrogen or $(A'-O)_xH$ in which A and A' are the same or different divalent alkylene having 2 to 4 carbons; and x and y are the same or different whole numbers from 1 to 100.

2. A composition according to claim 1 in which anion X is ethyl sulfate.

3. A composition according to claim 1 in which the said quaternary amine compound is lauryldimethylethylammonium ethyl sulfate.

4. An aqueous hair dye composition of the semi-permanent type comprising
   a. a tinctorial amount of a direct-dyeing nitroaminobenzene hair dye having good affinity for hair when applied at ambient temperatures;
   b. from about 0.1% to 3% by weight based on the total weight of the composition of a hair-substantive quaternary amine compound of formula:

(1) 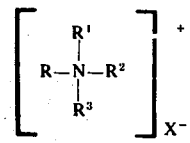

in which:
   i. $R^1$, $R^2$ and $R^3$ are alkyl having from 1 to 3 carbons;
   ii. R is long chain hydrocarbon having from 12 to 24 carbons; and
   iii. X is an anion selected from the group consisting of hydroxide, chloride, bromide, iodide, fluoride, sulfate, nitrate, methyl sulfate, phosphate, acetate and sulfonate; and
   c. from 0.2% to 3.5% by weight based on the total weight of the composition of a hair-substantive N-oxyalkylated fatty acid amide of formula:

(2) 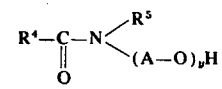

in which:
   i. $R^4$ is a long chain hydrocarbon having from 12 to 24 carbons;
   ii. $R^5$ is hydrogen or $(A'-O)_xH$ in which A and A' are the same or different divalent alkylene having 2 to 4 carbons; and $x$ and $y$ are the same or different whole numbers from 1 to 100.

5. A composition according to claim 4 wherein R of said quaternary amine compound contains 16 to 18 carbons.

6. A composition according to claim 5 wherein a mixture of quaternary amine compounds of formula (1) in claim 4 is contained in the composition.

7. A composition according to claim 4 wherein the N-oxyalkylated fatty acid amide is of the polyoxyethylated type of formula:

(3) 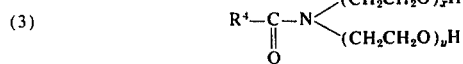

in which $R^4$ has the same value ascribed to it in claim 4 and $x$ and $y$ are whole numbers, the sum of $x + y$ being in the range of from 40 to 100.

8. A composition according to claim 4 wherein the nitroaminobenzene dye is $N^4,N^4$-bis(2'-hydroxyethyl)-$N^1$-methyl-2-nitro-p-phenylenediamine.

9. A composition according to claim 4 wherein the nitroaminobenzene dye is 1-anilino-4-amino-2-nitrobenzene.

10. A composition according to claim 4 wherein the nitroaminobenzene dye is N(2'-hydroxyethyl)-2-nitroaniline.

11. A composition according to claim 4 wherein the nitroaminobenzene dye is $N^1$-(2'-hydroxyethyl)-2-nitro-p-phenylenediamine.

12. A composition according to claim 4 wherein the nitroaminobenzene dye is N,N-bis(2'-hydroxyethyl)-2-amino-5-nitrophenol.

13. A composition according to claim 4 wherein the nitroaminobenzene dye is $N^1,N^4,N^4$-tris(2'-hydroxyethyl)-2-nitro-p-phenylenediamine.

14. A process for simultaneously dyeing conditioning hair which comprises applying the composition of claim 4 to hair and allowing said composition to remain in contact therewith for sufficient time to impart color to said hair and to condition the same whereby said hair becomes more manageable and there is an improvement in its sheen and texture.

15. An aqueous hair dye composition of the semi-permanent type comprising
   a. a tinctorial amount of a direct-dyeing nitroaminobenzene hair dye having good affinity for hair when applied at ambient temperatures;
   b. from about 0.1% to 3% by weight based on the total weight of the composition of a hair-substantive quaternary amine compound of formula:

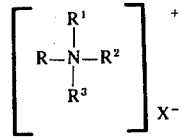

in which:
   i. $R^1$, $R^2$ and $R^3$ are alkyl having from 1 to 3 carbons;
   ii. R is long chain hydrocarbon selected from the group consisting of lauryl, myristyl, n-hexadecyl, oleyl, n-octadecyl, n-octadecenyl, n-octadecadienyl, arachidyl, behenyl and lignoceryl;
   iii. X is an anion selected from the group consisting of hydroxide, chloride, bromide, iodide, fluoride, sulfate, nitrate, methyl sulfate, phosphate, acetate and sulfonate; and
   c. from about 0.2% to 3.5% by weight based on the total weight of the composition of a hair-substantive N-oxyalkylated fatty acid amide of formula:

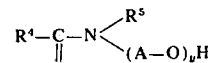

in which:
   i. $R^4$ is a long hydrocarbon selected from the group consisting of laurly, myristyl, palmityl, stearyl, behenyl, oleyl, linolyl, linolenyl; and
   ii. $R^5$ is hydrogen or $(A'—O)_xH$ in which A and A' are the same or different divalent alkylene having 2 to 4 carbons; and $x$ and $y$ are the same or different whole numbers from 1 to 100.

* * * * *